United States Patent [19]

Moret et al.

[11] 4,326,314
[45] Apr. 27, 1982

[54] ELECTRICALLY DRIVEN HAND-HELD APPARATUS FOR BODY CARE, IN PARTICULAR A TOOTHBRUSH OR MASSAGE APPARATUS

[75] Inventors: Michel-Antoine Moret, Chene Bourg; Pierre-Jean Jousson, Geneva, both of Switzerland

[73] Assignee: Les Produits Associes. LPA, Switzerland

[21] Appl. No.: 92,046

[22] Filed: Nov. 7, 1979

[30] Foreign Application Priority Data

Nov. 17, 1978 [CH] Switzerland ............... 11819/78

[51] Int. Cl.³ ........................ A46B 13/02
[52] U.S. Cl. ........................ 15/22 R; 74/48; 74/837; 128/62 A
[58] Field of Search ........... 15/22 R, 22 A, 22 C; 74/48, 70, 600, 837; 128/45, 46, 48, 49, 62 A; 51/170 R

[56] References Cited

U.S. PATENT DOCUMENTS 3,278,963  10/1966  Bond ................... 15/22 R

FOREIGN PATENT DOCUMENTS 2019003  11/1971  Fed. Rep. of Germany ..... 15/22 R
463457  11/1968  Switzerland ............. 15/22 R
485444  3/1970  Switzerland ............. 15/22 R
763032  12/1956  United Kingdom .
852376  10/1960  United Kingdom .
914844  1/1963  United Kingdom .
1021825  3/1966  United Kingdom .
1145590  3/1969  United Kingdom .
1228176  4/1971  United Kingdom .
1282004  7/1972  United Kingdom .
1307887  2/1973  United Kingdom .
1504626  3/1978  United Kingdom .

Primary Examiner—Edward L. Roberts
Attorney, Agent, or Firm—Kane, Dalsimer, Kane, Sullivan and Kurucz

[57] ABSTRACT

An electrically driven hand-held apparatus for body care, such as a toothbrush, operates by means of a rotating motor. An eccentric pin is driven by the motor and engages in a longitudinal slot defined by a fork which is secured to an instrument holder and in this manner sets the instrument holder supporting the treatment instrument such as the toothbrush in oscillatory motion about its longitudinal axis. In order to permit the oscillation amplitude to be adjusted without alteration of the oscillation frequency, the eccentric pin is fixed on a support inclined to its axis of rotation, the support being set in rotary motion by the motor shaft and the support being set in rotary motion by the motor shaft and the support being axially displaceable on its axis of rotation by means of an external operating knob. The effective eccentricity, that is to say the radial distance of the location of engagement in the longitudinal slot, of the eccentric pin from the axis of rotation of the support is thus variable.

19 Claims, 17 Drawing Figures

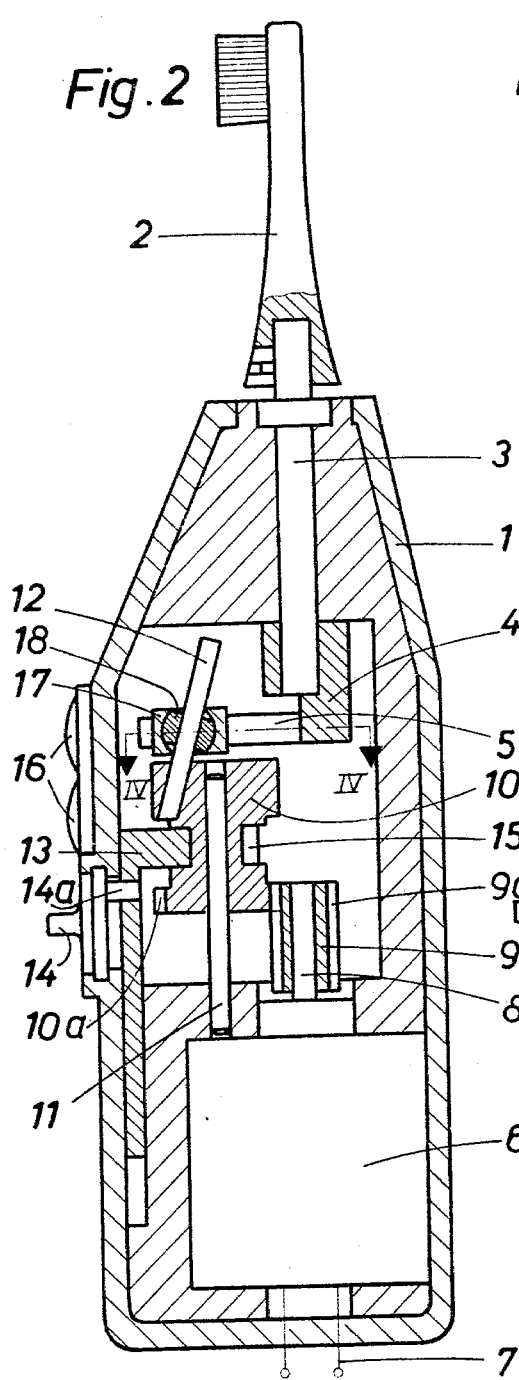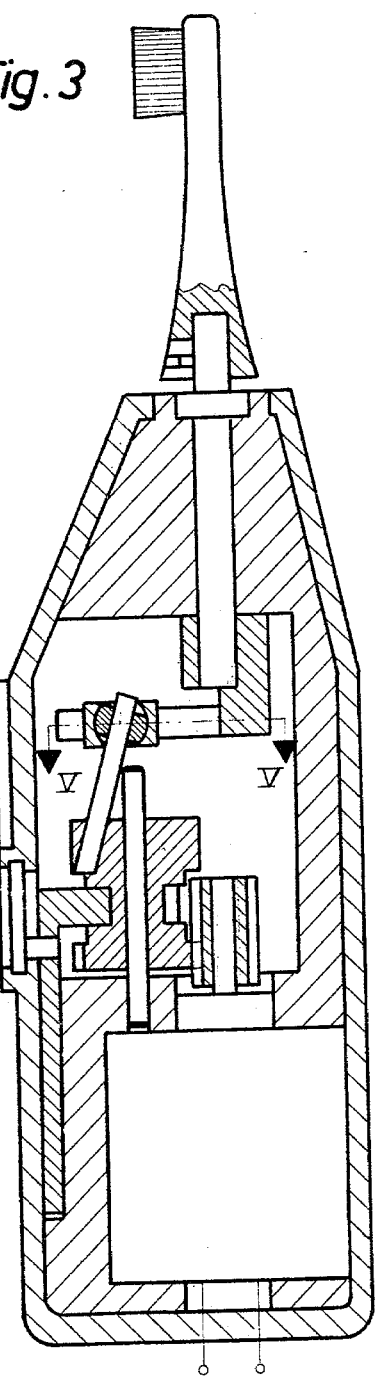
Fig. 2
Fig. 3

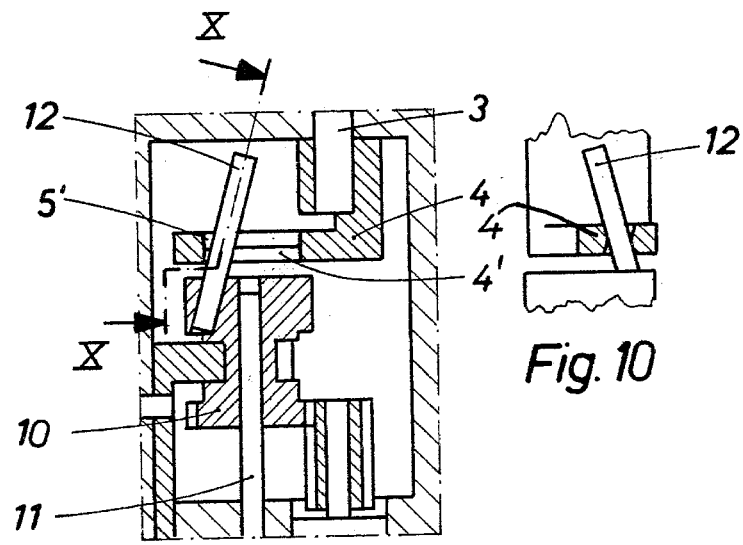
Fig. 10
Fig. 9
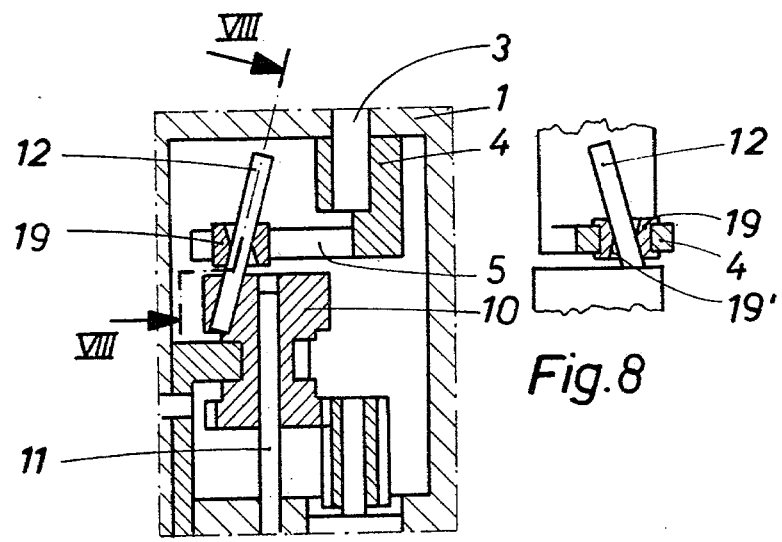
Fig. 8
Fig. 7

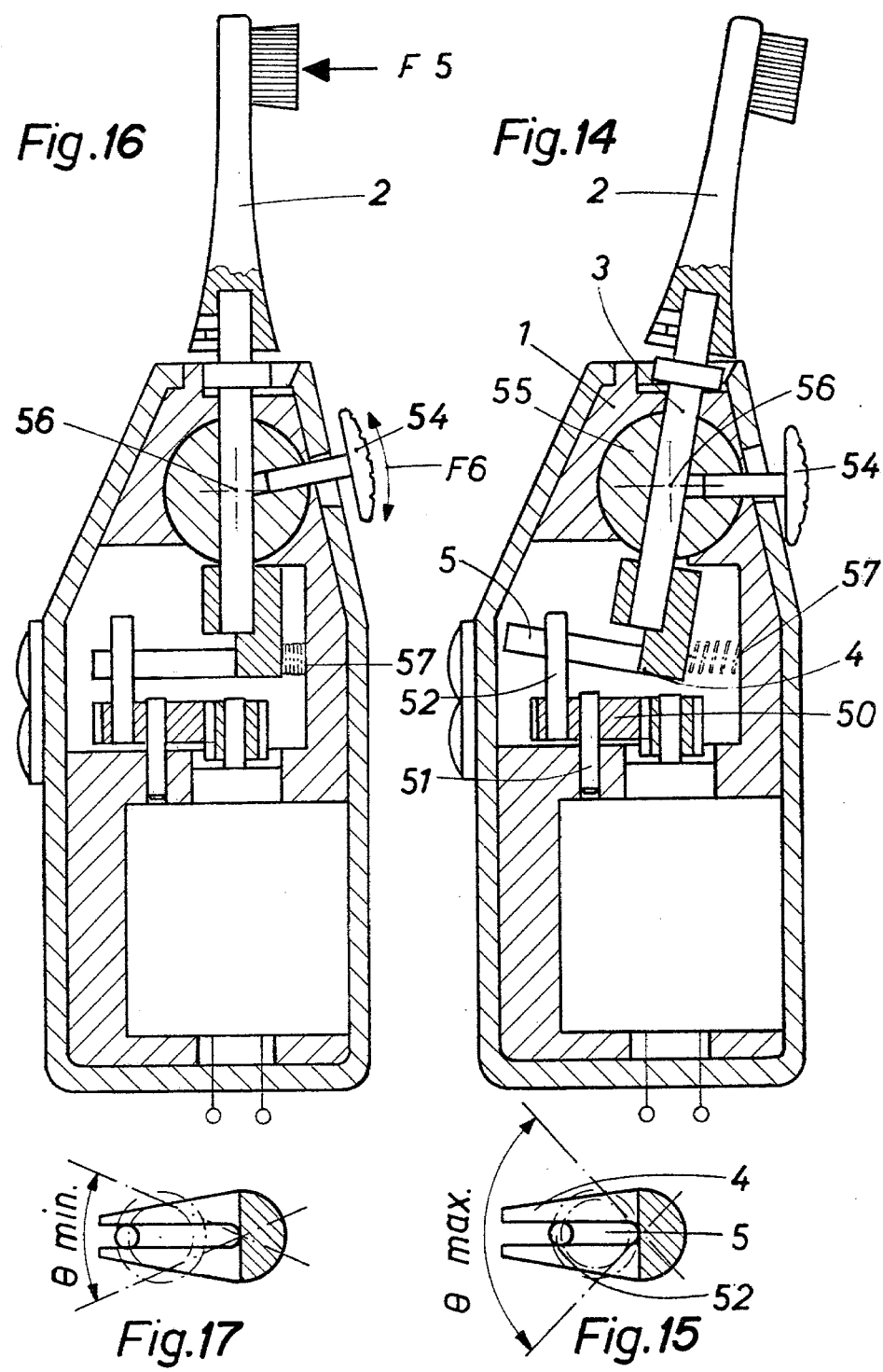

ELECTRICALLY DRIVEN HAND-HELD APPARATUS FOR BODY CARE, IN PARTICULAR A TOOTHBRUSH OR MASSAGE APPARATUS

BACKGROUND OF THE INVENTION

The present invention relates to an electrically driven hand-held apparatus for body care such as a toothbrush or a massage apparatus.

Known electrical toothbrushes of this kind have a direct current motor in the apparatus casing constructed in the form of a handgrip; the motor may be connected to the main supply network or may be fed from a battery, and its rotary motion is converted by means of a motion transformer to an oscillatory movement of the pushed-on toothbrush about its longitudinal axis. For this purpose a support in form of a disc provided with an eccentric pin is mounted on the motor shaft, and the inner end of the instrument holder has a radially extending fork attached thereto, the eccentric pin engaging between the arms thereof; the longitudinal axis of the instrument holder is radially offset relatively to the axis of rotation about which the eccentric pin circulates, that is to say relatively to the motor axis or the axis of rotation of the disc, respectively, in such a manner that the rotating eccentric pin affords the instrument holder with the toothbrush pushed thereon an oscillatory motion of constant oscillation amplitude about the shank of the toothbrush.

Such an oscillatory movement of the toothbrush is particularly effective for the care of teeth and mouth and permits above all an optimum message of the gums which is important for maintaining the health of the teeth and the gums; oscillation frequencies of the toothbrush of between approximately 40 and 60 Hz have been found most favourable for this purpose.

However, experience has shown that the sensitivity of the gums and the teeth to the brushing or the message, respectively, differs widely from person to person, and in particular in the case of a gum disease, above all paradontosis, injuries and bleeding may occur even by careful brushing with a normal brush. The pain threshold, also, is very different individually. In order to take account of these individual physiological conditions, the user of an electrical toothbrush heretofore had in general only the possibility to use attachable toothbrushes with sufficiently soft bristles, and he had to take care that he did not press the brush down too hard. A reduction of the supply voltage of the motor would have the unfavourable consequence of a reduction of the rotary speed of the motor and thus a reduction of the oscillation frequency of the brush, thereby disadvantageously affecting the message effect; moreover the gums would be stressed as before in as much as it is squeezed to and fro through a path corresponding to the unchanged oscillation amplitude; when the gums are sensitive or diseased, this may lead to tearing the tissue even at a relatively low message frequency.

A reduction of the mechanical energy or output of the oscillating treatment instrument without reduction of the oscillation frequency is frequently desirable even for general body massage apparatus, in order to be able to perform appropriately careful massages of sensitive or inflamed body regions or for example for the purpose of make-up.

An electrical toothbrush of the kind described above is already known, in which a change of the distance between the longitudinal axis of the instrument holder and the axis of rotation of the support for the eccentric pin is provided, so that thereby the oscillation amplitude can be adjusted within certain limits. This is attained by the fact that either the motor with the disc supporting the eccentric pin is mounted in the casing in a radially displaceable manner, or that the eccentric pin is located on a gearwheel which is mounted adjacent the motor shaft on a bearing plate and which meshes with a pinion secured on the motor shaft, and the entire bearing plate can be rotated about the motor shaft. However, the first mentioned construction with a radially displaceable motor necessitates a complicated constructional design of the apparatus, in which case additionally the diameter of the apparatus casing must be correspondingly increased in an unfavourable manner; likewise the rotatable mounting of the entire bearing plate with the gearwheel carrying the eccentric pin in accordance with the other known constructional form and the necessary arrangement of the operating element for the adjustment of the bearing plate are very unfavourable in a constructional respect, and furthermore, upon displacement of the bearing plate in the peripheral direction of the casing, obviously also the rest position of the toothbrush, or the entire angular range of the toothbrush oscillation is twisted relatively to the apparatus casing, respectively; this renders convenient manipulation of the apparatus difficult.

SUMMARY OF THE INVENTION

The invention is to provide a hand-held apparatus of the kind referred to above in which the problem of changing the oscillation amplitude of the treatment instrument without influence upon its oscillation frequency is solved in a constructionally considerably simpler manner than heretofore and in which the user can adjust the oscillation amplitude easily without reduction of the convenient manipulation.

The main advantage of the hand-held apparatus according to the invention resides in that for the purpose of changing the oscillation amplitude merely the degree of eccentricity of the eccentric pin must be variable in relation to the axis of rotation of its support, so that neither a radial displaceability of the motor, nor a bearing plate rotatable about the motor shaft must be provided on which a gearwheel is mounted which carries the eccentric pin and is driven by the motor shaft. In a particularly advantageous and simple constructional form of the hand-held apparatus according to the invention the eccentric pin is orientated on its support inclined to the axis of rotation thereof and this support is displaceably mounted in the direction of its axis of rotation, that is to say simply along its axis of rotation. This permits a continuous change of the oscillation amplitude by simple axial displacement of the support; this can be realised easily by means of a simple external operating element. In this case the support for the eccentric pin may conveniently be a gearwheel which is mounted in a rotatable and axially displaceable manner on a stub parallel to the motor shaft and which meshes with a pinion fixed on the motor shaft.

The support of the eccentric pin may be displaceable in a stepwise manner. In addition, the pin may include sections which are radially offset in a stepwise manner to permit stepwise adjustment of the oscillation amplitude. Means for guiding the eccentric pin are provided. Means may also be provided for permitting the adjustment of two different oscillation amplitudes.

Another constructional solution for changing the oscillation amplitude is based on a possibility to tilt the entire instrument holder, so that the inner end thereof with the fork which embraces the eccentric pin is adjustable in relation to the axis of rotation of the eccentric pin support. Finally even an automatic amplitude adjustment may be provided as a function of the loading exerted upon the treatment instrument.

The invention is not limited only to hand-held apparatus with a rotating motor, but is also usable for hand-held apparatus, in particular electrical toothbrushes with a swinging armature motor which, upon connection to the alternating current mains supply network oscillates directly at the supply network frequency; heretofore the instrument holder of these hand-held apparatus is fixed directly to the swinging armature in the axial extension thereof. The construction in accordance with the invention permits now even hand-held apparatus with a swinging armature motor to be constructed in such a manner that for the first time the oscillation amplitude is variable in a simple manner, in that the swinging armature drives the support with the eccentric pin in an oscillating manner and the instrument holder is mounted independently of the swinging armature. Thus in this case a change of the oscillation amplitude of the instrument holder substantially does not influence the oscillation amplitude of the swinging armature itself, for which the swinging armature motor is dimensioned and adjusted; this is extremely advantageous. If, in contrast, the feed voltage would be reduced, for example for the purpose of a more careful treatment, the motor torque would be reduced in an unfavourable manner.

BRIEF DESCRIPTION OF THE DRAWINGS

The invention is explained in detail by means of constructional examples with reference to the drawings. There are shown in.

DETAILED DESCRIPTION OF THE INVENTION

Figure 1:
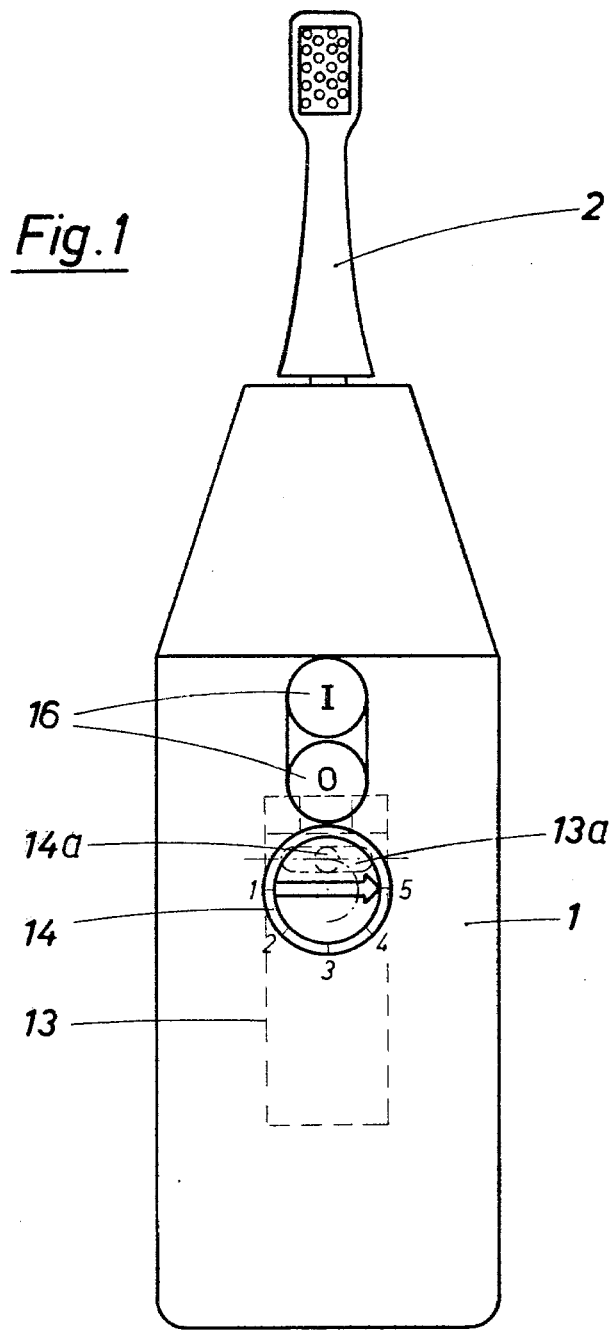
FIG. 1 a side view of a hand-held apparatus according to the invention in the form of an electrical toothbrush, FIG. 2 an axial section through the hand-held apparatus according to FIG. 1 with an adjustable eccentric pin which assumes its position corresponding to the greatest swing angle, FIG. 3 the hand-held apparatus according to FIG. 2 in the eccentric position which corresponds to the smallest swing angle, FIG. 4 a section on the line IV—IV in FIG. 2, FIG. 5 a section on the line V—V in FIG. 3, FIG. 6 a section on the line VI—VI in FIG. 4, FIG. 7 a section through the parts essential for the invention, of a first variant of the example according to FIGS. 1 to 6, FIG. 8 a section on the line VIII—VIII in FIG. 7, after rotation of the eccentric pin through 90°, FIG. 9 a section through the parts essential for the invention, of a second variant of the example according to FIGS. 1 to 6, FIG. 10 a section on the line X—X in FIG. 9, after rotation of the eccentric pin through 90°, FIG. 11 the axial section through a second constructional form in which the oscillation amplitude is variable automatically as a function of the loading exerted upon the treatment instrument, FIG. 12 the section through the parts essential for the invention of a third constructional form with the possibility of a stepwise adjustment of the oscillation amplitude, FIG. 13 the diagrammatic illustration of the essential parts of a fourth constructional form with a rocker member supporting two eccentric pins, FIG. 14 the axial section through a fifth constructional form with a tiltable instrument holder which assumes its position corresponding to the largest swing angle, FIG. 15 a diagrammatic view from above upon the fork comprising the longitudinal slot and the eccentric pin according to FIG. 14, FIG. 16 the constructional form according to FIG. 14 in the position of the instrument holder corresponding to the smallest swing angle, and FIG. 17 a diagrammatic view from above upon the fork comprising the longitudinal slot with the eccentric pin according to FIG. 16.

According to FIGS. 1 to 3, the hand-held apparatus comprises a casing 1 with a push-on toothbrush 2 interchangeably attached to an instrument holder 3. The instrument holder 3 in the form of a shaft is mounted in the casing 1 in a manner rotatable about its longitudinal axis, and at its inner end it carries a fork 4 with the longitudinal slot 5 between the two arms thereof which are orientated radially in relation to the longitudinal axis of the instrument holder 3 and the casing 1.

Furthermore, an electro-motor 6 which is illustrated merely diagrammatically, is accommodated in the casing 1 and involves preferably a direct current motor; it is connectable to the current supply by means of the terminals 7; in the case of an alternating current mains supply network, obviously a rectifier is additionally provided. A hand-held apparatus fed from a battery or an accumulator may also be involved.

Figure 4:
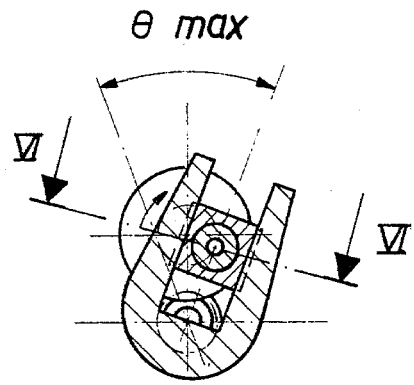
Figure 6:
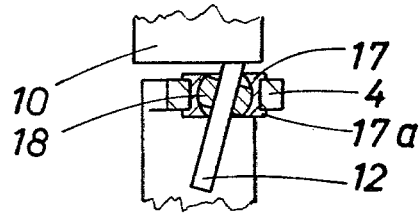

A pinion 9 is non-rotatably mounted on the motor shaft 8 and has peripheral teeth 9a which mesh with the peripheral teeth 10a of a rotation-symmetrical substantially cylindrical support 10. This support 10 is mounted rotatably and freely displaceably in an axial direction on a stub 11 which is parallel to the motor shaft 8; it supports an eccentric pin 12 on its side facing the fork 4. The longitudinal axis of this eccentric pin 12 is orientated inclined to the axis of rotation of the support 10, that is to say also to the stub 11 and is so dimensioned and arranged that it does not intersect the extension of the stub 11. The eccentric pin 12 extends in a freely displaceable manner through the diametrical bore of a ball 18 of a ball joint which forms a guide member 17 which is freely displaceable within the longitudinal slot 5 of the fork 4. As indicated in FIGS. 4 and 6, the two sides facing the fork arms, of the joint bearing of the guide member 17 comprise flanges 17a which engage on both sides over these fork arms, so that the guide member 17 is retained in the longitudinal slot displaceable along the fork 4.

The middle region of the support 10 is provided with a ring groove 15 (FIG. 2) into which engages the radially orientated limb of an L-shaped slider member 13 the other limb of which is axially displaceably mounted at the inside of the outer wall of the casing 1 and comprises a transverse slot 13a (FIG. 1). The slider member 13, and thus also the support 10 with the eccentric pin 12 can be displaced axially in relation to the axis of rotation thereof by means of an external operating element 14 in the form of a rotary knob (FIG. 1) to the inside of which a stub 14a is attached which engages into the transverse slot 13a of the slider member 13, so that because of the inclined position of the eccentric pin 12 the location of engagement thereof in the longitudinal slot 5 and thereby the effective eccentricity is changed.

Two water-tight push-buttons 16 for switching the electromotor 6 on and off are provided above the operating element.

When the motor is running, the support 10 and thus also the eccentric pin 12 is set in a rotary motion about the stub 11, so that the fork 4 driven by the eccentric pin 12 and thereby the instrument holder 3 carrying the push-on toothbrush in a non-rotatable manner perform an oscillating movement about its longitudinal axis. For this purpose the arrangement is obviously made so that the circle described by the engagement point of the eccentric pin 12 in the longitudinal slot 5 lies outside the longitudinal axis, or the swing axis, respectively, of the instrument holder 3. The rotary speed of the motor and the reduction gear ratio of the drive have been selected such that the oscillation frequency amounts to at least approximately 50 Hz.

Figure 5:
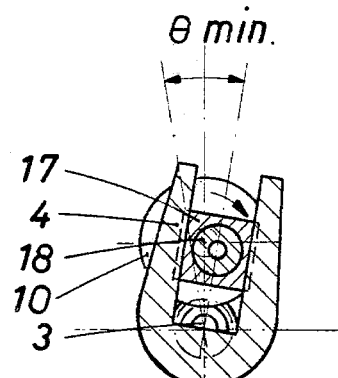

The swing angle, or the oscillation amplitude, respectively, of the instrument holder 3 and thus also that of the toothbrush 2 is the smaller, the smaller is the radial spacing between the axis of rotation of the eccentric pin 12 and the location of engagement thereof in the longitudinal slot 5. Since because of the inclination under consideration of the eccentric pin 12 in accordance with FIGS. 2 and 3 this radial spacing is greatest in the forwardly displaced position of the support 10 in which it is disposed closest to the longitudinal slot 5, this position illustrated in FIG. 2 of the eccentric pin 12 corresponds to the greatest swing angle $\theta_{max}$ (FIG. 4) which is fixed preferably to a value between 40° and 60°, for example 50°. The other end position of the support 10 illustrated in FIG. 3 in which it assumes its position furthest away from the longitudinal slot 5, corresponds to the minimum swing angle $\theta_{min}$ (FIG. 5) which advantageously amounts to only from 10° to 20°, for example 15°. According to FIG. 1 five different positions of the eccentric and thus also oscillation amplitudes and swing angles, respectively, are marked on the periphery of the operating element 14, in order to facilitate the adjustment which may be performed continuously.

In the variant according to FIGS. 7 and 8, the guide member 19 which is displaceable in the longitudinal slot 5 of the fork 4 and which is penetrated by the eccentric pin 12, consists of a bush with a double-conical inner peripheral wall 19' which widens out to both ends of the bush and the cone angle of which is adjusted to the inclined orientation of the eccentric pin 12, so that the latter may slide satisfactorily in the bush 19.

In the variant illustrated in FIGS. 9 and 10, no guide member is provided for the eccentric pin 12 which engages directly in the longitudinal slot 5 closed in this case, of a member 4 fixed to the instrument holder 3. The walls 4' limiting the longitudinal slot 5' are profiled in a double-conical manner corresponding to the inclination of the eccentric pin 12 lying against them.

The remaining construction of the examples illustrated in FIGS. 7 and 8, and FIGS. 9 and 10, respectively, corresponds to the constructional example according to FIGS. 1 to 6.

Figure 11:
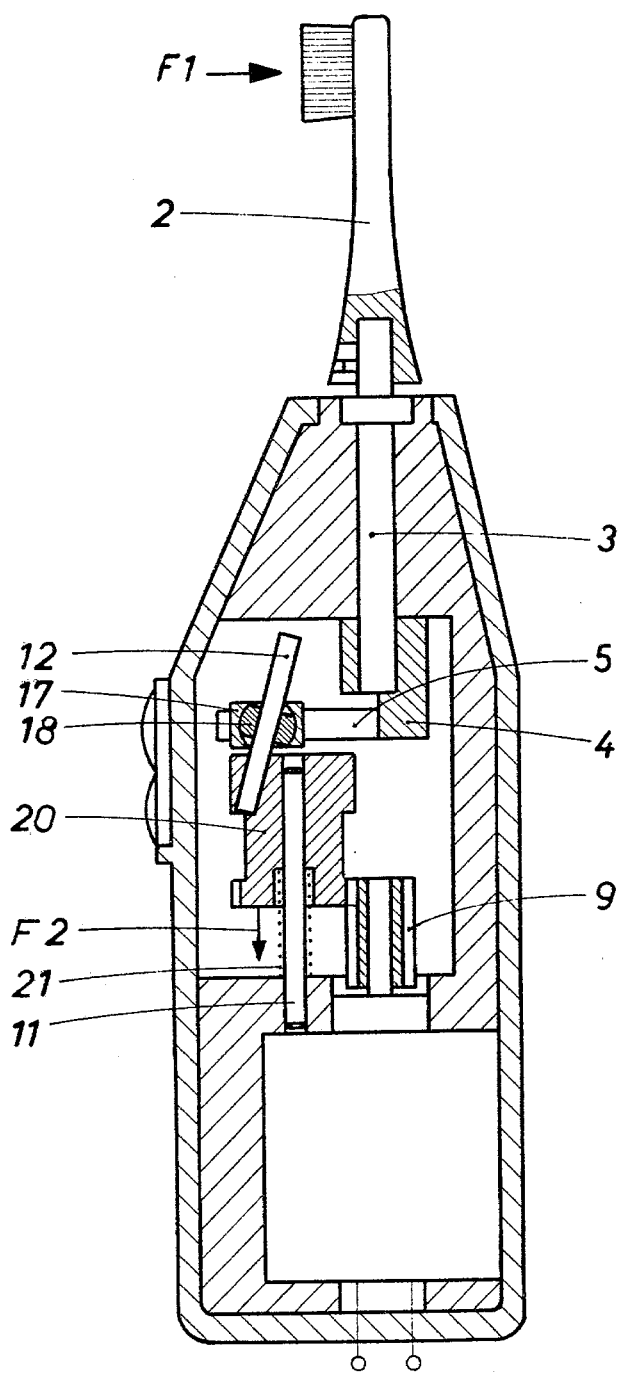

The constructional example according to FIG. 11 does not comprise an external operating element for adjusting the support 20 with the eccentric pin 12, but is provided with a return spring 21 which surrounds the stub 11 and which normally retains the support 20 in its forward position illustrated in FIG. 11, which corresponds to the largest oscillation amplitude of the toothbrush 2, as explained with reference to the first constructional example. As in this constructional example according to FIGS. 1 to 6, the eccentric pin 12 extends through the ball 18 of a guide member 17 which is constructed in the form of a ball joint and which is displaceable in the longitudinal slot 5 of the fork 4 attached to the instrument holder 3. When during the use of the handheld apparatus a force is exerted on the bristles of the toothbrush 2 in the direction of the arrow F1, a reaction force is exerted by the limiting wall of the longitudinal slot 5 or the diametrical bore of the ball 18, respectively, upon the eccentric pin 12, which force has an axial component because of the inclined position of the said pin. This has as a consequence an automatic axial displacement of the support 20 in the sense of the arrow F2 against the effect of the return spring 21, this displacement being the greater the more the toothbrush 2 is being loaded, i.e. the more the user presses the toothbrush against the teeth or the gums. It is attained in this way that the oscillation amplitude of the toothbrush decreases automatically with increasing loading and consequently the risk of injury is reduced. Upon relieving the toothbrush of the load, the eccentric pin 12 assumes again its normal position corresponding to the largest oscillation amplitude under the effect of the return spring 21. Under certain circumstances the automatic reduction of the oscillation amplitude described can be combined with the constructional form according to FIGS. 1 to 6 in such a manner that additionally a retaining or locking device is provided on the operating element 14 and the desired position of the eccentric pin 12 after external adjustment thereof is fixed thereby, in order that this position does not change under the effect of the spring 21. When the user desires an automatic adjustment of the oscillation amplitude to the pressing force exerted by the brush, it is merely necessary for him to release the retaining or locking device, whereupon the spring 21 becomes effective again.

Figure 12:
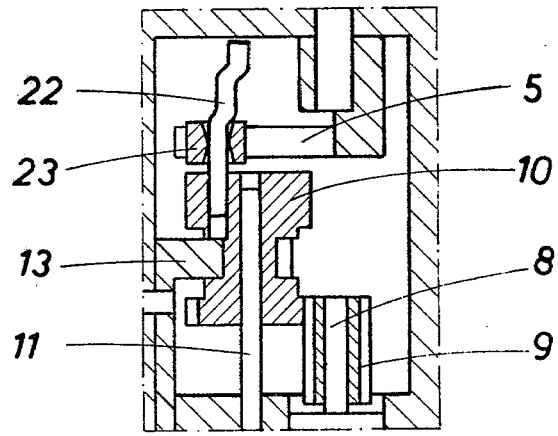

In the constructional example according to FIG. 12, the eccentric pin 22 comprises sections which are radially offset in stepwise manner in relation to its longitudinal axis or its axis of rotation, respectively, and extends through a bush which serves as a guide member 23 in the longitudinal slot 5 and which has a convexly inwardly curved inner peripheral wall. The remaining construction of this constructional example corresponds to the example according to FIGS. 1 to 6. Thus the eccentric pin 22 is again located on a support 10 which is driven by the motor shaft 8 and which is axially displaceable from the outside on its stub 11 by means of a slider member 13; in the example under consideration this adjustment occurs in a stepwise manner. The magnitude of the effective eccentricity and thus the oscillation amplitude depends in this case upon the fact which one of the radially offset regions of the eccentric pin 22 is located within the longitudinal slot 5 or the guide member 23, respectively, the convexly curved inner wall of which permits the easy displacement of the deformed eccentric pin 22.

Figure 13:
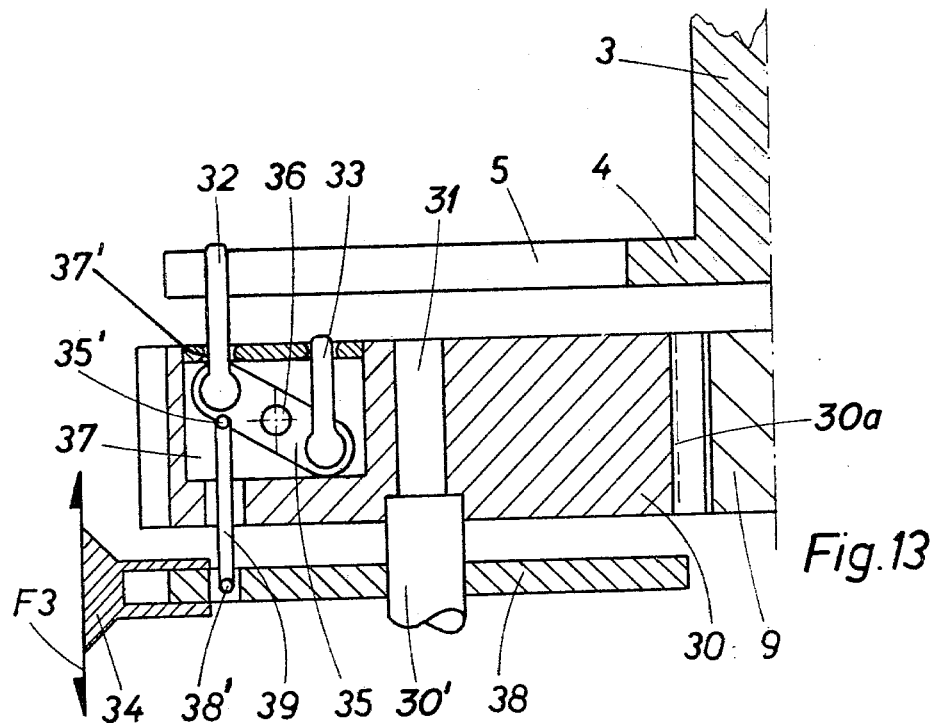

In the constructional example according to FIG. 13, two eccentric pins 32 and 33 are attached to the ends of a rocker member 35 which is mounted in a recess 37 of the support 30 and is rotatable about the tipping axis 36 which is orientated perpendicular to the axis of rotation of the said support. The support 30 has peripheral teeth 30a which mesh with the pinion 9 on the motor shaft, and when the motor runs it is set in rotary motion about the stub 31. The rocker member 35 is disposed radially and eccentrically in relation to the stub 31, so that the two eccentric pins 32 and 33 have different spacings from their common axis of rotation formed by the stub 31. In the position illustrated in FIG. 13, of the rocker member 35 the eccentric pin 32 located at a larger distance from the the stub 31 engages in the longitudinal slot 5 of the fork 4 at the instrument holder 3 and thereby defines the larger oscillation amplitude of the treatment instrument; in the other position of the rocker member 35 in which the latter is rotated about the tipping axis 36 in a clockwise direction in accordance with FIG. 13, the eccentric pin 33 engages in the longitudinal slot 5, so that then the instrument holder 3 swings with the smaller oscillation amplitude. In order that the two eccentric pins 32 and 33 maintain always at least approximately their position parallel to the stub 31, they project with sufficient play through openings 37' which are provided in a plate which covers the recess 37. For the purpose of displacing the rocker member 35 there serve a disc 38 which rotates together with the support 30 and is arranged underneath it in an axially displaceable manner, and a small rod 39 which extends with sufficient play through an opening in the bottom of the recess 37; the one end of the rod 39 is pivotally attached to the rocker member 35 at 35', its other end being pivotally attached to the disc 38 at 38'. An external operating element 34 the inner fork-shaped end of which engages around the edge of the disc 38, can be displaced in the sense of the double-arrow F3 and thereby drives the disc 38 which is non-rotatably and axially displaceably arranged on a sleeve 30' which is secured on the support 30 and which is rotatably mounted on the stub 31.

Furthermore, in FIG. 13 the arrangement is made so that the two eccentric pins can never engage simultaneously in the longitudinal slot 5, or the rocker member cannot come to standstill in a position in which both eccentric pins engage in the longitudinal slot, respectively. In other words, when the rocker arm 35 is parallel to fork 4, neither of pins 32, 33 is within the slot 5. Moreover a return spring not illustrated is provided which when the motor is switched off moves the instrument holder with the fork 4 with displacement of the rocker member, to a middle rest position in which the rocker member can be switched over without difficulty.

The constructional form illustrated in FIGS. 14 to 17 comprises an instrument holder 3 which is mounted rotatable about its longitudinal axis, in a diametrical bore of a pivot pin 55 and which furthermore is mounted tiltable about a tipping axis 56 by means of this pivot pin 55 within the casing 1, the tipping axis 56 being orientated perpendicular to the longitudinal axis of the instrument holder 3 as well as also the fork 4 fixed to its inner end and having the longitudinal slot 5. The eccentric pin 52 engaging in the longitudinal slot 5 again is seated on a support 50 which is set in rotary motion about the stub 51 by the motor shaft and extends parallel to its axis of rotation. By means of an external operating element 54 which is secured to the pivot pin 55, the instrument holder 3 with the push-on toothbrush 2 attached thereto may be swung through a certain angle in the sense of the double-arrow F6 between the first position illustrated in FIG. 14 and the second position illustrated in FIG. 16. In the first position in which in the example under consideration the instrument holder 3 is inclined relatively to the longitudinal axis of the casing, the radial distance of the eccentric pin 52 from the longitudinal axis, or the swing axis, respectively, of the instrument holder 3 is smallest and therefore the swing angle $\theta_{max}$ (FIG. 15) is greatest. In the second position (FIG. 16) the radial spacing referred to is greatest and therefore the swing angle $\theta_{min}$ (FIG. 17) is smallest. Spring 57 presses with its inner end against fork 4 whereby it is allowed to slide relative to said fork 4 when support 50 rotates. Instrument holder 3 with the fork 4 oscillates about the holder axis. Under certain circumstances the instrument holder 3 may be fixed in every position selected, by means of a retaining device not illustrated.

In a modified constructional form the instrument holder 3 is held normally, with the treatment instrument not loaded, in a position corresponding to the largest swing angle (FIG. 14) by means of a return spring 57 illustrated by a broken line. The treatment instrument, or the push-on toothbrush, respectively, may then be pushed on in such a way that the pressing force exerted during the treatment in the sense of the arrow F5 according to FIG. 16 rotates the instrument holder in the direction of the position corresponding to the smallest swing angle, against the effect of the return spring 57. In this case in which an external operating element 54 may be omitted, the reduction of the oscillation amplitude occurs therefore automatically, as in the constructional example according to FIG. 11, as a function of the pressing force exerted by the user.

The invention is not limited to the constructional examples illustrated, but permits manifold variants in respect of the construction of the individual parts. Furthermore, the features according to the invention, in particular the embodiments according to FIGS. 1 to 12, are applicable without difficulties to hand-held apparatus with a swing armature motor, in order that in these apparatus, too, the oscillation amplitude of the instrument holder separated from the swing armature may be varied in a simple manner.

What is claimed is:

1. An electrically driven hand-held apparatus for body care such as a toothbrush or massage apparatus, comprising an instrument holder which is adapted for the attachment of a treatment instrument and which is drivable for oscillation about its longitudinal axis, a motor, a rotatably mounted support driven by the motor, an eccentric pin which is secured to the support, an inner part of the instrument holder defining a longitudinal slot which slot extends substantially radially in respect of the longitudinal axis of the instrument holder and in which the eccentric pin engages in a freely displaceable manner, and means for varying the distance between the axis of rotation of said support and the location of engagement of said eccentric pin in the longitudinal slot.

2. An apparatus according to claim 1, in which the eccentric pin is orientated on its support and inclined to the axis of rotation of the latter, the support being mounted for displacement in the direction of its axis of rotation.

3. An apparatus according to claim 2, in which the support for the eccentric pin is rotatably and axially displaceably mounted on a stub which is parallel to a shaft of the motor and comprises peripheral teeth which mesh with the teeth of a pinion which is fastened on the motor shaft.

4. An apparatus according to claim 3, in which a guide member for the eccentric pin is freely displaceably mounted within the longitudinal slot and comprises a ball joint with a ball which possesses a diametrical bore penetrated by the eccentric pin.

5. An apparatus according to claim 3, in which a guide member for the eccentric pin is freely displaceably mounted within the longitudinal slot and comprises a bush with a double-conical inner peripheral wall which widens towards both ends of the bush and the cone angle of which is adjusted to the inclined orientation of the eccentric pin.

6. An apparatus according to claim 3, in which the walls of the holder defining the longitudinal slot are profiled in a double-conical manner corresponding to the inclination of the eccentric pin engaging them.

7. An apparatus according to claim 1, in which the eccentric pin comprises sections which are radially offset in a stepwise manner in respect of its longitudinal axis and its support is displaceable in a stepwise manner in the direction of its axis of rotation.

8. An apparatus according to claim 7, in which the support for the eccentric pin is rotatably and axially displaceably mounted on a stub which is parallel to a shaft of the motor and comprises peripheral teeth which mesh with the teeth of a pinion which is fastened on the motor shaft.

9. An apparatus according to claim 7, in which a guide member for the eccentric pin is mounted within the longitudinal slot in a freely displaceable manner, the said guide member being in the form of a bush having a convexly inwardly curved inner peripheral wall.

10. An apparatus as defined in claim 7 including a guide member positioned within said slot, said eccentric pin extending through said guide member.

11. An apparatus according to claim 1 including means for adjusting the position of the support in the direction of its axis of rotation.

12. An electrically driven hand-held apparatus for body care, such as a toothbrush or massage apparatus, comprising an instrument holder which is adapted for the push-on attachment of a treatment instrument and which is drivable to oscillate about its longitudinal axis, a motor, a rotatably mounted support driven by the motor, an eccentric pin which is secured to the support, and an inner member of the instrument holder defining a longitudinal slot which slot extends substantially radially in respect of the longitudinal axis of the instrument holder and in which the eccentric pin engages in a freely displaceable manner, the instrument holder being mounted for tipping movement about an axis which is orientated perpendicular to its longitudinal axis as well as also substantially perpendicular to the longitudinal direction of the longitudinal slot, so that when the instrument holder is tipped the radial spacing between the longitudinal axis thereof and the axis of rotation of the support for the eccentric pin is variable.

13. An apparatus according to claim 12, in which a substantially cylindrical section of the instrument holder is mounted in a diametrical bore of a cylindrical pivot pin which in turn is rotatable about its axis of rotation which forms the tipping axis for the instrument holder.

14. An apparatus according to claim 12 including means for tipping said instrument holder about said axis perpendicular to its longitudinal axis.

15. An apparatus according to claim 14 including a casing; a pivot pin pivotally mounted within said casing, said pivot pin having a bore therein, said instrument holder mounted within said bore, and an operating element secured to said pivot pin, said operating element located external to said casing.

16. An apparatus according to claim 12 including a return spring urging said instrument holder to a position corresponding to the largest oscillation amplitude of said instrument holder.

17. An apparatus according to claim 16 wherein said return spring and instrument holder are positioned such that a force exerted in a particular direction perpendicular to the longitudinal axis of said instrument holder opposes the force of said return spring.

18. An electrically driven hand-held apparatus for body care, comprising an instrument holder which is adapted for the attachment of a treatment instrument and which is drivable for oscillation about its longitudinal axis; a motor; a rotatably mounted support driven by said motor; a pair of eccentric pins mounted at the ends of a rocker member which is mounted to said support, the rocker member being tiltable about an axis which is perpendicular to the axis of rotation of said support; an inner part of said instrument holder defining a longitudinal slot extending substantially radially with respect to the longitudinal axis of said instrument holder, one of said eccentric pins engaging said slot when said rocker member is tilted to a first position, the other of said eccentric pins engaging said slot when said rocker member is tilted to a second position.

19. An electrically driven hand-held apparatus for body care such as a toothbrush or massage apparatus, comprising:
an instrument holder adapted for the attachment of a treatment instrument and which is drivable for oscillation about its longitudinal axis;
a motor;
a rotatably mounted support driven by the motor, said support mounted for displacement along its axis of rotation;
an eccentric pin secured to the support, said pin inclined with respect to the axis of rotation of said support;
an inner part of the instrument holder defining a longitudinal slot which extends substantially radially with respect to the longitudinal axis of the instrument holder, said eccentric pin engaging said slot; and
a return spring urging said support to a position along its axis of rotation which corresponds to the largest oscillation amplitude of the instrument holder,
said instrument holder, support, eccentric pin, and inner part arranged such that when a force perpendicular to the longitudinal axis of said instrument holder is applied in a particular direction, a reaction force is exerted by a wall of said inner part defining said slot, said reaction force being exerted upon said eccentric pin which, in turn, exerts a force on said support opposing the force exerted by said spring.

* * * * *